United States Patent [19]
Abele et al.

[11] Patent Number: 6,010,480
[45] Date of Patent: *Jan. 4, 2000

[54] BALLOON CATHETER

[75] Inventors: John E. Abele, Concord; Ronald A. Sahatjian, Lexington, both of Mass.

[73] Assignee: Boston Scientific Corporation, Natick, Mass.

[*] Notice: This patent is subject to a terminal disclaimer.

[21] Appl. No.: 08/899,104

[22] Filed: Jul. 23, 1997

Related U.S. Application Data

[60] Division of application No. 08/609,274, Mar. 1, 1996, Pat. No. 5,746,745, which is a continuation-in-part of application No. 08/441,603, May 15, 1995, Pat. No. 5,693,014, which is a continuation of application No. 08/110,655, Aug. 23, 1993, abandoned.

[51] Int. Cl.$^7$ .................................................. A61M 29/00
[52] U.S. Cl. .............................. 604/96; 604/265; 606/194
[58] Field of Search .............................. 604/96, 101, 102, 604/103, 172, 265, 280, 523; 606/191–198; 128/DIG. 14, DIG. 21

[56] References Cited

U.S. PATENT DOCUMENTS

| | | | |
|---|---|---|---|
| 5,026,607 | 6/1991 | Kiezulas | 604/265 X |
| 5,049,131 | 9/1991 | Deuss | 604/265 |
| 5,250,070 | 10/1993 | Parodi | 604/96 |
| 5,693,014 | 12/1997 | Abele et al. | 604/96 |

*Primary Examiner*—Ronald K. Stright, Jr.
*Attorney, Agent, or Firm*—George A. Herbster; Pearson & Pearson

[57] ABSTRACT

An expansible balloon catheter has at least a first exterior surface with a given coefficient of friction and a second exterior surface with a greater coefficient of friction. In a compact form only the first exterior surface is exposed to produce one coefficient of friction during transfer of the collapsed or uninflated balloon to and across a lesion. When inflated, the second surface dominates the first surface and produces a second coefficient of friction.

16 Claims, 5 Drawing Sheets

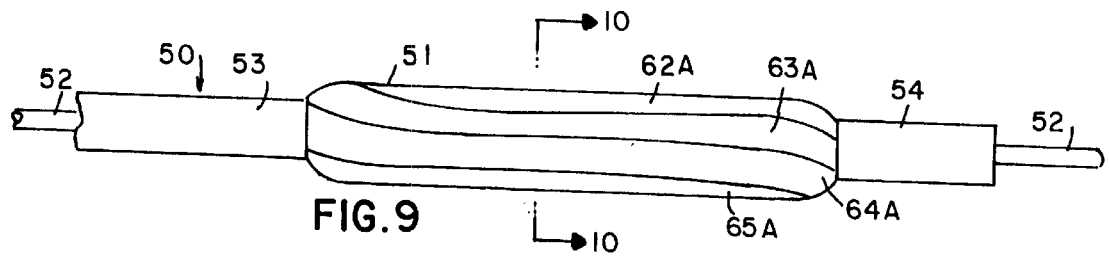
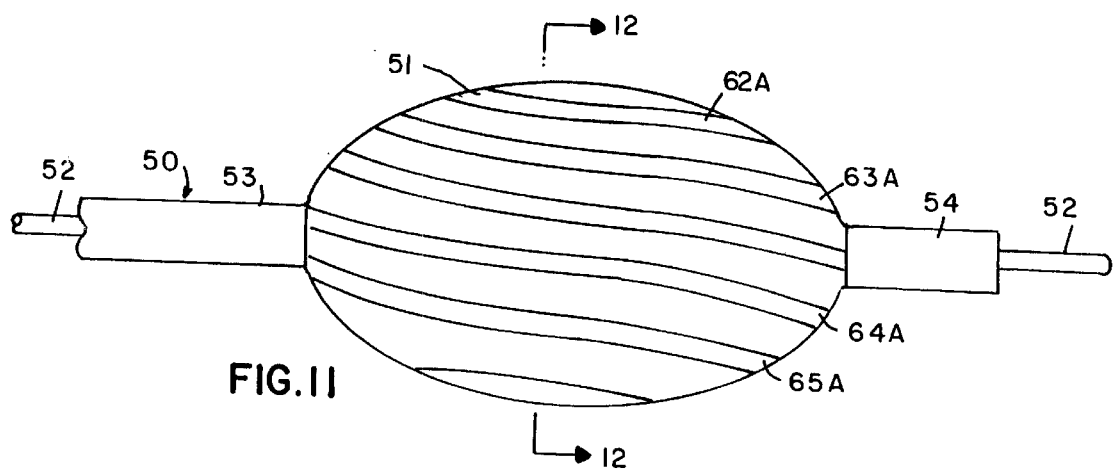
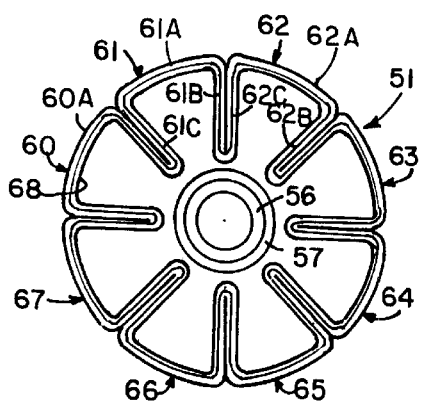
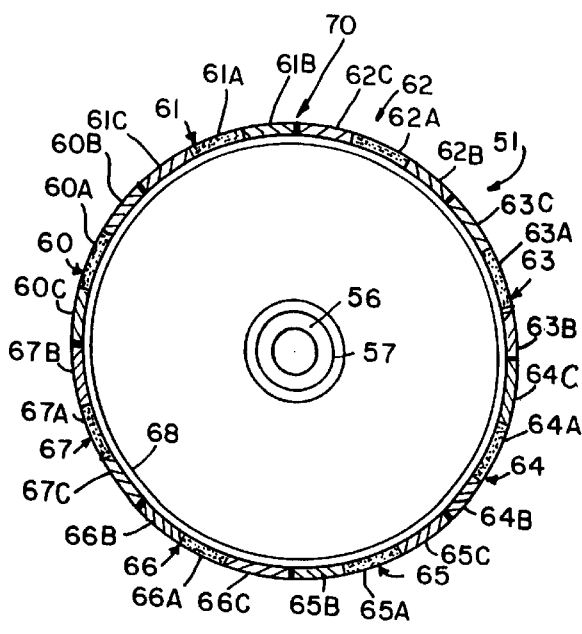

BALLOON CATHETER

CROSS REFERENCE TO RELATED APPLICATION

This application is a division of application Ser. No. 08/609,274 filed Mar. 1, 1996, now U.S. Pat. No. 5,746,745 granted May 5, 1998 which is a continuation-in-part of application Ser. No. 08/441,603 filed May 15, 1995, now U.S. Pat. No. 5,693,014 granted Dec. 2, 1997 which is a continuation of Ser. No. 08/110,655 filed Aug. 23, 1993.

BACKGROUND OF THE INVENTION

1. Field of the Invention

This invention generally relates to balloon catheters and more particularly to the structure of and method of manufacture of balloon catheters.

2. Description of Related Art

Coronary balloon angioplasty involves the steps of inserting a deflated balloon into a coronary artery, advancing the balloon across a lesion until the balloon is centered at the lesion and then inflating the balloon to dilate and remove the stenosis. Significant efforts have been directed toward constructing balloons with smaller cross sections so that they can better cross a tight lesion. However, experience with these smaller balloon catheters has highlighted two desirable, but until now antithetical, characteristics. First, the balloon should exhibit very low coefficient of sliding friction to facilitate initial positioning with minimal trauma. Secondly the balloon should exhibit longitudinal or axial stability during and after inflation. This stability is needed to overcome any tendency for forces exerted by the adjacent tissue to displace or shift the balloon longitudinally in the vessel. Independent efforts have been undertaken to address the issues of sliding friction and of positional stability. However, no activities seem to have been directed toward the development of a balloon that incorporates both characteristics in a single device.

For example, Boston Scientific Corporation, the assignee of this invention, manufactures a Slider™ PTCA Catheter having a lubricous, bonded coating covering the exterior of the balloon. This facilitates access to a lesion and enhances the ability of the balloon to cross the lesion.

Similarly the following patents disclose other coatings adapted for use with balloon catheters:

| | |
|---|---|
| 4,810,543 | (1989) Gould et al. |
| 5,026,607 | (1991) Kiezulas |
| 5,049,131 | (1991) Deuss |
| 5,102,402 | (1992) Dror et al. |

U.S. Pat. No. 4,810,543 to Gould et al. discloses articles having low friction surfaces and processes for producing such articles. Specifically the Gould et al. patent proposes treating a surface with a mixture of concentrated sulfuric acid and a low molecular weight polyhydroxy compound and removing any excess treating mixture.

U.S. Pat. No. 5,026,607 to Kiezulas discloses a method in which a protective compound, such as urethane, is coupled with a slip additive, such as siloxane and, optionally, a crosslinking agent for a protective compound such as a polyfunctional aziridine, coats the surface of medical apparatus. After setting, the material provides a lubricous surface that is tough and flexible and particularly adapted for use with balloon catheters.

U.S. Pat. No. 5,049,131 discloses a balloon catheter that can be enlarged from a first predetermined diameter to a second predetermined diameter without completely withdrawing the catheter from a body passage. In this patent it is suggested that the folds of the balloon be filled with a substance, such as a paste, that has a therapeutic or medicinal effect.

U.S. Pat. No. 5,102,420 to Dror et al. discloses a balloon catheter with an exterior coating of body effecting chemicals. In some embodiments a balloon is inflated, dusted with microcapsules containing a drug and then of deflated prior to entry into the patient. Alternately, cusps, folds and other corrugations are formed when the balloon is deflated and capture microcapsules containing the drug material. These microcapsules are then presented when the balloon is inflated.

Each of the Gould et al. and Kiezulas patents discloses methods and procedures for making a device more lubricous. However, none describes any method or procedure for improving axial stability.

The following patents describe balloons that incorporate stabilizing structures to enhance the positioning, engagement and retention of a balloon at a lesion:

| | |
|---|---|
| 4,447,227 | (1984) Kotsanis |
| 4,896,669 | (1990) Bhate et al. |
| 4,921,484 | (1990) Hillstead |
| 4,927,412 | (1990) Menasche |
| 4,986,830 | (1991) Owens et al. |
| 5,002,531 | (1991) Bonzel |

U.S. Pat. No. 4,447,227 to Kotsanis discloses multipurpose medical devices. Each device has a stabilizing structure for enhancing positioning, engagement and retention of the balloon in a desired lumen. The stabilizing structure is in the form of an additional medical grade balloon or one or more vacuum responsive members, such as active or passive microsuckers.

U.S. Pat. No. 4,896,669 to Bhate et al. discloses a dilation catheter with an outer tubular balloon portion. This balloon portion has circumferential crimps at each of two end transitions and an intermediate axially extended portion with longitudinal crimps. The balloon portion expands readily to a predetermined diameter while undergoing little change in length. Stability is provided because the transition portions are capable of longitudinal extension in response to minor longitudinal contraction at the two ends of the balloon portion to reduce axial movement of the balloon portion. This characteristic is stated to reduce axial movement when the balloon is inflated.

U.S. Pat. No. 4,921,484 to Hillstead discloses a mesh balloon catheter device, analogous to an expandable stent, in which the catheter has a distal end with a tube of woven interlaced filaments forming a tubular mesh. The proximal end of the mesh can be moved toward the distal end of the mesh to expand the mesh into surrounding tissue. This particular structure is designed for location in a bladder where the mesh holds the catheter in place while allowing an obstructed fluid flow.

U.S. Pat. No. 4,927,412 to Menasche discloses a catheter adapted for use in a coronary sinus where the sinus walls are slippery, extensible and tapered in a distal direction. Prior catheters normally were subject to axial displacement while being inflated. In accordance with this patent a balloon has a truncated conical surface with outwardly facing, spaced apart, parallel concentric lands for frictionally engaging the coronary sinus. This structure is stated to provide a high retentive force for stabilizing the catheter and preventing its ejection from the coronary sinus.

U.S. Pat. No. 4,986,830 to Owens et al. discloses a valvuloplasty catheter with a balloon that remains positionally stable during inflation. Stability is achieved by providing first and second inflation ports of differing sizes so that the expanding member inflates to create a dog-bone effect that allows the balloon to surround and stabilize the expander member relative to the valve being treated.

U.S. Pat. No. 5,002,531 to Bonzel discloses an inflatable balloon with a hose-like outer skin to which is connected at axially oriented edges and an inner skin also having a hose-like shape. The outer skin acts as a holding membrane. In this particular structure, the inner skin is elastic and undergoes a considerable reduction in diameter when the balloon is deflated. This eases passage of the catheter as it is advances through or retracts from an artery.

Each of the foregoing references therefore proposes some structure for improving axial stability during inflation. Although the Bonzel patent recognizes a need for easing passage through a lesion, neither it nor any other of these references describe any method or procedure for making a balloon more lubricous. Consequently the prior art defined by these references can be characterized as providing either reduced friction when a balloon is deflated or increased friction when a balloon is expanded, but not both.

It has also been suggested that balloons be used for the purpose of carrying a stent to a vessel and for the purpose of expanding that stent. The following United States Letters Patents disclose examples of such structures:

| | |
|---|---|
| 4,681,110 | (1987) Wiktor |
| 4,732,152 | (1988) Wallsten et al. |
| 4,950,227 | (1990) Savin et al. |
| 5,026,377 | (1991) Burton et al. |

U.S. Pat. No. 4,681,110 to Wiktor discloses a catheter arrangement with a main tubing that contains a radially expandable liner and a member for moving the liner out of the tubing so that the liner can expand radially outward to engage a vessel wall.

U.S. Pat. No. 4,732,152 to Wallsten et al. discloses a device and method for implanting a prothesis or stent in which the prothesis is held in a radially contracted state by the device. An expandable chamber within the device permits relative movement between the elements of the devices as to permit the prothesis to be inserted and radially expanded in the location.

U.S. Pat. No. 4,950,227 to Savin et al. discloses a stent delivery system in which a stent is positioned around the distal portion of a catheter and is sized in the retracted condition to closely surround the catheter. A sleeve extends over the margin of the stent and catheter. The catheter and stent are cooperatively constructed and arranged so that expansion of the catheter to its expanded state causes expansion of the stent including the margin of the stent from its contracted condition to its expanded condition.

U.S. Pat. No. 5,026,377 to Burton et al. discloses an instrument for the deployment or retraction of a self-expanding stent in a body canal. An elongated tubular outer sleeve includes an elongated inner core movable relative to the sleeve. The core has a grip member formed at or near its distal end that is adapted to releasably hold a self-expanding stent within the outer sleeve.

In each of the foregoing patents, a structure is provided to rigidly position a device corresponding to a contracted stent on the distal end of the catheter in a fixed position so that the stent or similar device does not move relative to the end of the catheter as the distal end passes through the body to a final site. These structures complicate stent delivery systems and their use.

SUMMARY

Therefore it is an object of this invention to provide an improved balloon that facilitates placement at a lesion and yet retains its position at the lesion during inflation.

Still another object of this invention is to provide an improved balloon catheter that exhibits different frictional characteristics in its inflated and non-inflated states.

Yet another object of this invention is to provide a balloon catheter that has a low coefficient of sliding friction in a deflated state and a higher coefficient of friction in a inflated state.

Still yet another object of this invention is to provide a balloon catheter that has a high coefficient of sliding friction in a deflated state for facilitating the transport of a contracted stent and a lower coefficient of friction in an inflated or expanded state.

In accordance with one aspect of this invention a medical balloon is formed of a thin material for expansion from a compact state to an expanded state in a patient's vessel. The balloon is formed with a first material portion or spaced first material portions such that the balloon in its compact state essentially exposes the exterior surfaces of only the first material portion or portions. In the expanded state the balloon exposes the exterior surfaces of both the first and remaining material portions for contact with surrounding vessels. The exterior surface on a first material portion has an integral surface with a coefficient of friction that differs from the coefficient of friction of the exterior surface of a remaining portion of the balloon.

In accordance with another aspect of this invention a stent delivery system includes a catheter with an inflation lumen, and a medical balloon formed of a thin material positioned at the distal end of the catheter in communication with the inflation balloon so the balloon is expansible from a compact state to an expanded state in response to the injection of an inflation fluid through the inflation lumen. A first material portion or a plurality of first spaced material portions are located so that the balloon essentially exposes the exterior surfaces of only the first material portion or portions in its compact state. As the balloon expands, it expands the stent and exposes the exterior surfaces of the first material portion and of the remaining material portion.

The exterior surface of a first material portion has a coefficient of friction that is greater than the coefficient of friction of the exterior surface of the remaining portion of the balloon, such that the balloon in its compact state engages and provides friction to hold the stent in place on the balloon and in its expanded state facilitates the release of the balloon from the stent.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 9 depicts the application of this invention to an alternative form of a balloon catheter and is a front plan view of the balloon catheter in an uninflated or compact state;

FIG. 10 is a section taken along lines 10—10 in FIG. 9;

FIG. 11 is a front plan view of the balloon catheter in FIG. 9 in an inflated or expanded state;

FIG. 12 is a section taken along lines 12—12 in FIG. 10;

DESCRIPTION OF ILLUSTRATIVE EMBODIMENTS

Figure 1:
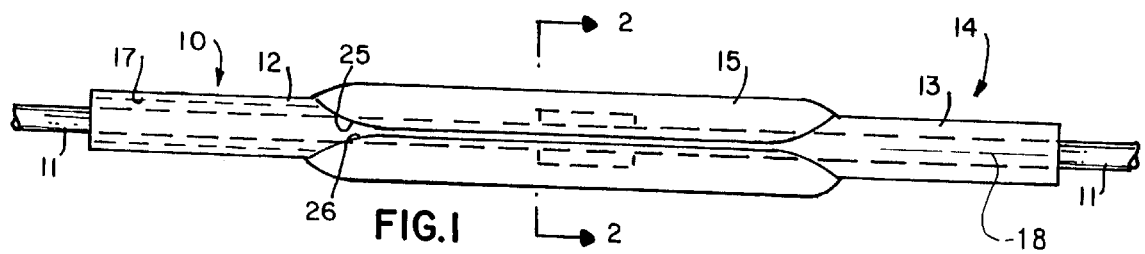
FIG. 1 is a front plan view of a portion of a balloon catheter constructed in accordance with this invention in an uninflated or compact state.

In the embodiment of FIGS. 1 through 4, a catheter 10 slides over a guidewire 11 and includes tubular portions 12 and 13 at a distal end 14 of the catheter 10. A balloon 15 lies longitudinally between and attaches to the tubular portions 12 and 13. Ports 16, shown in phantom in FIG. 3, allow fluid to be admitted to the area of the balloon 15 for expansion. The fluid is supplied either through a lumen 17, in FIG. 1 that carries the guidewire 11 or through an auxiliary lumen (not shown), all is well known in the art.

Figure 2:
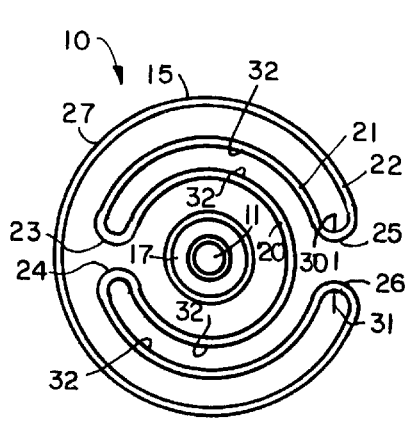
FIG. 2 is a cross-section taken along lines 2—2 in FIG. 1.

FIGS. 1 and 2 depict the disposition of thin balloon material about the catheter 10 and an axis 18 in a compact position. For clarity, FIG. 2 depicts the material out of scale in spaced adjacent layers. In an actual balloon the 5 layers would be tightly packed. The balloon 15 is formed in three concentric layers including an inside layer 20, and intermediate layer 21 and an outer layer 22. The intermediate layer 21 folds back over the inside layer 22 such that the folds 23 and 24 are circumferentially adjacent on the back side of the balloon 15. The intermediate layer 21 and outer layer 22 produce adjacent folds 25 and 26 as shown in FIGS. 1 and 2.

In accordance with this invention, a first integral exterior surface portion, or surface 27, of the outer layer 22 between points marked by the intersection of the axes 30 and 31 with the folds 25 and 26, respectively, is treated to have a first coefficient of sliding that facilitates transferring the balloon 15 across a lesion. The second or remaining integral exterior surface 32 has a greater coefficient of sliding friction. As will be apparent, the second surface portion, or surface 32, angularly displaced from the first exterior surface 27, also has a greater surface area than the first surface 27.

Figure 3:
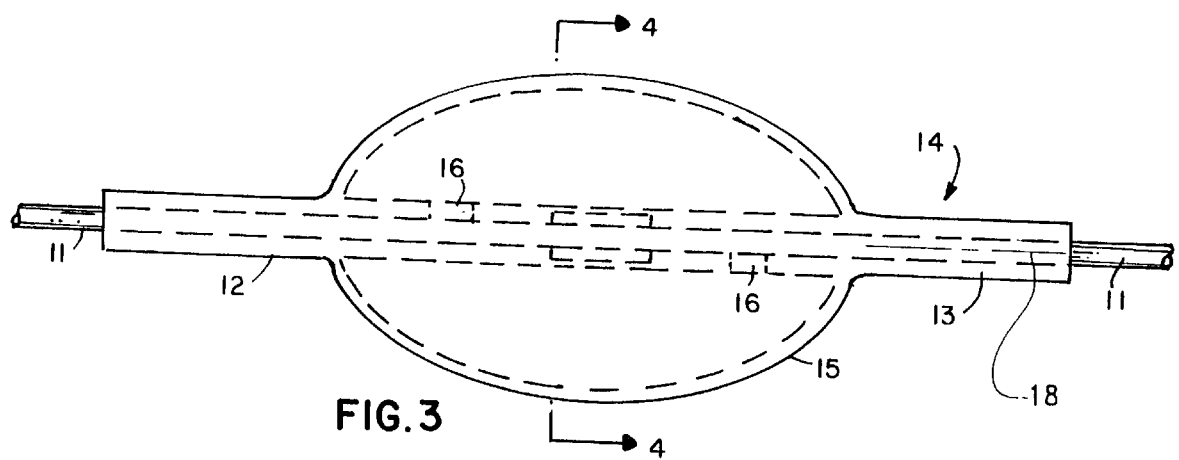
FIG. 3 is a front plan view of the balloon catheter in FIG. 1 in an inflated or expanded state.
Figure 4:
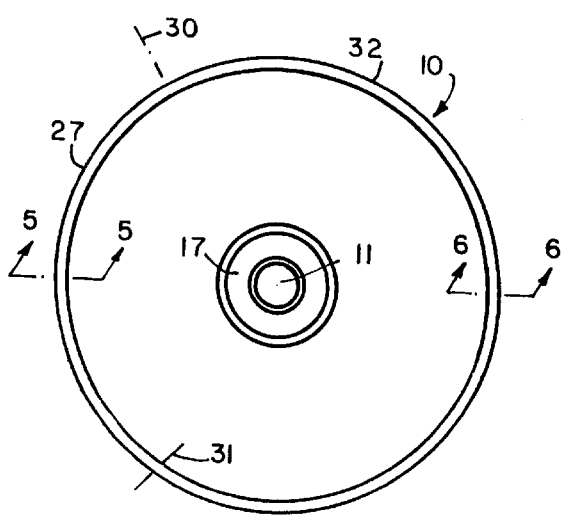
FIG. 4 is a cross-section taken generally along lines 4—4 in FIG. 3.

When the balloon 15 expands to the configuration shown in FIGS. 3 and 4, all of the exterior surfaces 27 and 32 are exposed. However, the second surface 32 with its greater coefficient of friction and greater area dominates, so it increases the overall coefficient of friction for the expanded balloon 15 and is substantially determinative of the overall friction exerted by the balloon 15 against any adjacent vessels. Thus the coefficient of friction for the entire balloon 15 in its expanded form is greater than the coefficient in the collapsed or compact form. Consequently, the balloon 15 exhibits different coefficients of friction in its compacted and expanded forms. If the exterior surface 27 is treated to reduce its coefficient of friction, the balloon 15 has a low coefficient of sliding friction in its compact form that facilitates its placement at a lesion. As the balloon 15 expands, its overall coefficient of friction increases as the surface 32 is exposed, so the balloon 15 retains its position within a patient's vessel during and after inflation.

Figure 5:
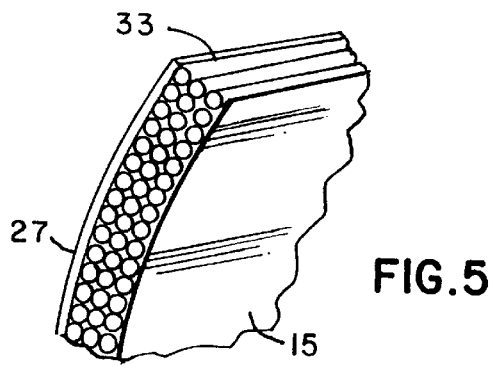
FIG. 5 is an enlarged cross-section taken along lines 5—5 in FIG. 4.
Figure 6:
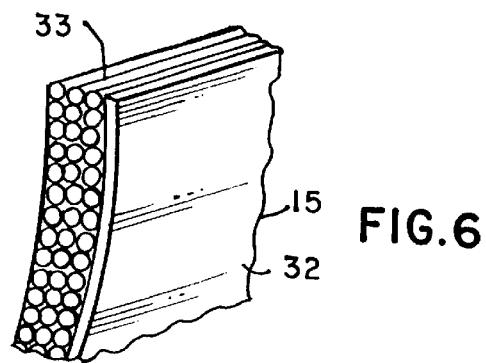
FIG. 6 is an enlarged cross-section taken along lines 6—6 in FIG. 4.

There are several methods and structures for producing integral surfaces or portions of different coefficients of friction. FIGS. 5 and 6, for example, disclose portions of the balloon catheter in FIG. 4 corresponding to the first surface 27 in FIG. 5 and the second surface 32 in FIG. 6 in which the balloon 15 has a cellular or tubular honeycomb core 33. In accordance with one method, the balloon, during manufacture, is expanded in the form shown in FIGS. 3 and 4 and coated with diverse coatings over portions coextensive to the surfaces 27 and 32. The first surface 27 would be coated with a material that optimizes lubricousness while the surface 32 would be coated with a material that has a higher coefficient of friction. After the coating cures and becomes integral with the balloon 15, the balloon is collapsed and folded into the form shown in FIGS. 1 and 2. Coatings for the first surface 27 include those composed of hydrogel, silicone and hydrophilic oil materials. The second surface 32 could remain uncoated or be formed of a tacky coating, such as a polyurethane coating or even be coated with the same material as the first surface 27 that is roughened after application.

Figure 7:
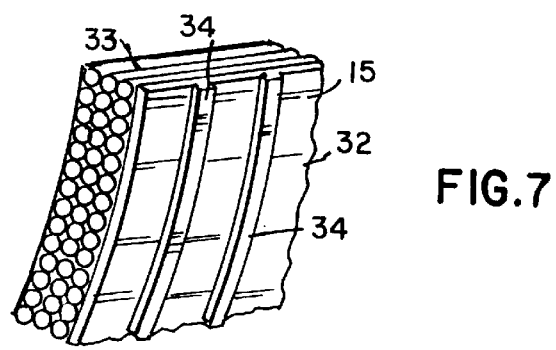
FIG. 7 depicts an alternate embodiment of the structure shown in FIG. 6.

FIG. 7 shows another embodiment of a balloon 15 in which the surface 32 is textured by forming circumferentially extending, axially spaced ribs 34. The ribs 34 can press gently into and anchor with surrounding tissue as the balloon 15 expands. This effectively provides an overall coefficient of friction that is greater than the coefficient of friction of a smooth surface 27.

Figure 8:
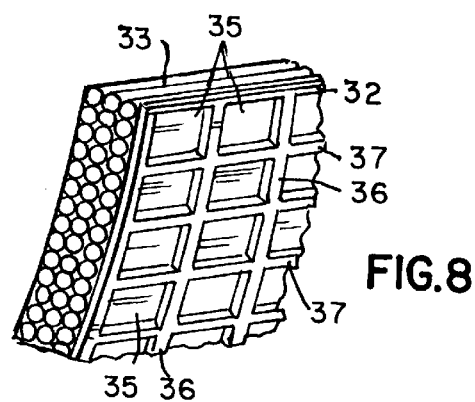
FIG. 8 shows still another alternative embodiment of the structure shown in FIG. 6.

FIG. 8 depicts another embodiment in which the surface 32 is treated with an array of molded pockets 35 bounded by circumferentially and longitudinally extending ribs 36 and 37. When expanded this waffle-like surface gently contacts adjacent tissue and anchors the balloon 15 in place. In either of the embodiments of FIGS. 7 or 8, the material forming the surfaces 32 and 27 may be the same. The ribs 34 in FIG. 7 and the ribs 36 and 37 in FIG. 8 would be coextensive only with the surface 32. In accordance with one manufacturing process, a slippery coating, such as a hydrogel material, would be applied to the entire surface of the balloon. Then a material etching process, such as laser etching, would form the ribs 34 or ribs 36 and 37 by removing the intermediate portions of the coating.

FIGS. 9 through 12 depict a balloon catheter assembly 50 with an expandable balloon 51 that extends to a distal end over a guidewire 52. Spaced tubular portions 53 and 54 of the catheter 50 support the balloon 51. The catheter is generally similar to that shown in respect to FIGS. 1 through 4.

In this particular embodiment, however, the balloon 51 is compacted by pleating. More specifically, when the balloon 51 deflates, it forms into pleats, eight pleats in this example, about a central tube 56 interconnecting the tubular portions 53 and 54 and a centrally disposed marker 57. The pleats 60 through 67 shown in FIGS. 9 and 10 are laminated structures with a base film 68 and a plurality of coatings. Specifically the pleat 60 includes a central coating 60A that is at the outer surface of the compacted balloon 51 and that is coextensive longitudinally with the balloon 51. Likewise the pleats 61 through 67 have corresponding central, exteriorly exposed, longitudinal sections 61A through 67A. Each of these surface sections 60A through 67A has a low coefficient of friction. These are essentially the only surface sections that are exposed when the balloon 51 is in a compact form.

When the balloon 51 expands about the central tube 56 as shown in FIGS. 11 and 12, the pleats 60 through 67 open into a generally circular configuration, depending of course on the tissue into which the balloon 51 expands. At pleat 60, this exposes areas 60B and 60C on either side of the central area 60A. Similarly, areas 61B through 67B and 61C through 67C are exposed on opposite sides of the central areas 61A through 67A respectively. Each of the areas 60B through 67B and 60C through 67C has a higher coefficient of friction than the surfaces of coatings 60A through 67A respectively. Moreover, the total area of the areas 60B through 67B and 60C through 67C exceeds the total area of the areas 60A through 67A.

In FIG. 12, radial lines, such as radial line 70, depict the boundary between areas such as areas 61B and 62C. In actual practice the areas 61B and 62C would be formed as a continuous coating. The radial line 70 and other similar radial lines are shown for purposes of description only.

As will be apparent, surface treatment as shown and described with FIGS. 7 and 8 can be used in the surfaces 60B through 67B to achieve angularly spaced surface portions of a greater coefficient of friction. Moreover, the embodiment shown in FIGS. 9 through 12, like the embodiment shown in FIGS. 1 through 4, provides a balloon catheter that has different coefficients of friction in its compact and expanded forms. Thus, like the embodiment of FIGS. 1 through 4, the embodiment in FIGS. 9 through 12 facilitates its placement at a lesion. Further, this embodiment also retains its position during inflation because its overall coefficient of friction increases during inflation. This embodiment differs from that shown in FIGS. 1 through 4 because in FIGS. 9 through 12 the balloon has plural surfaces of differing coefficients of friction rather than one area of each coefficient of friction.

In another specific embodiment, an uncoated balloon 15 as shown in FIG. 1 is folded into the form shown in FIG. 2, albeit more compactly form. An integral coating then is applied to the balloon 15 in a conventional manner as described, for example, in U.S. Pat. No. 5,091,205 issued Feb. 25, 1992 describing hydrophilic lubricous coatings. The entire exterior surface 27 of the balloon 15 is coated when the balloon 15 is compacted as shown in FIG. 2. When the balloon 15 expands to the form shown in FIG. 3, the coating remains limited to the surface 27. The surface 32 remains uncoated and provides a surface of greater friction.

Figure 13:
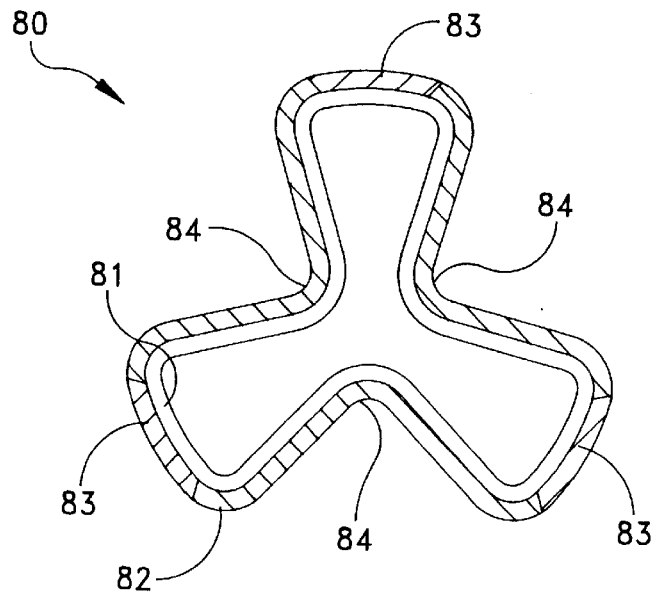
FIGS. 13 and 14 are cross sections of an alternate form of a expansible device that incorporates this invention.
Figure 14:
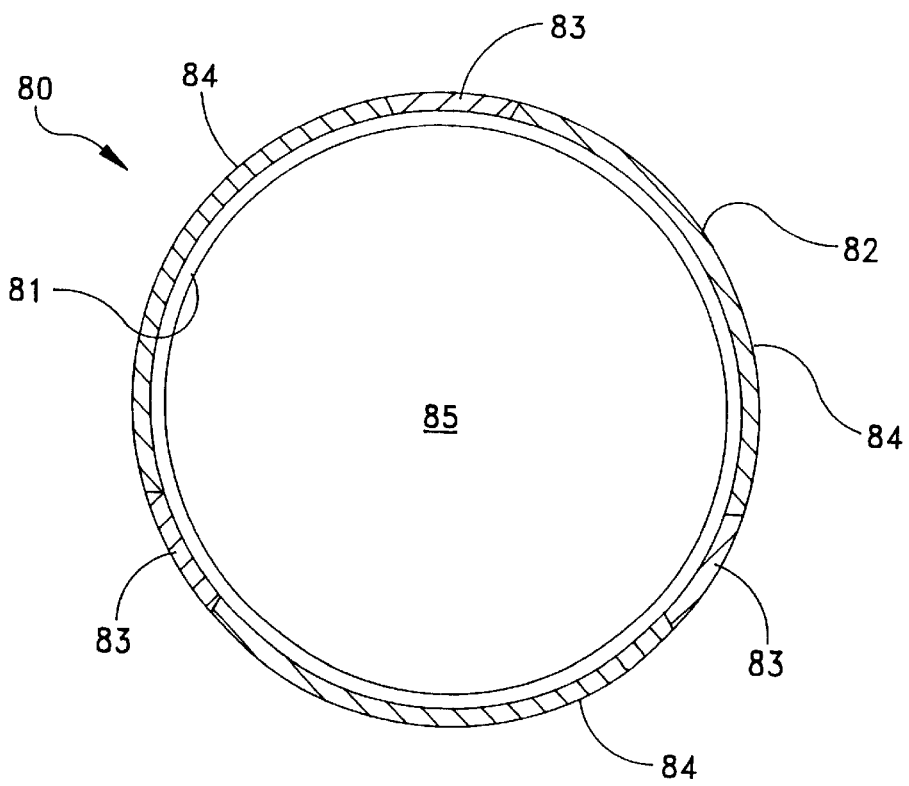

FIGS. 13 and 14 disclose an alternative version of an expansible device 80 formed of two laminations. An inner lamination 81 could comprise a material that tends to return to its original folded shape when the balloon deflates and the outer lamination, generally designated 82, by an integral surface coating having first material portions 83 and second material portions 84 to produce different frictional characteristics over their respective surfaces. As shown in FIG. 13 the expansible device 80 is in a original, relaxed form such that the expansible device 80 presents only the first portions 83 for contact with any vessels whereby the frictional characteristics of the coatings 83 essentially determine the frictional characteristics of the expansible device 80 in the compacted form. The portions 84 are displaced radially inward.

Once the device 80 is positioned appropriately within a vessel in the compact form shown in FIG. 13, an inflation fluid can be delivered through a structure such as shown in FIGS. 1 and 2, to pressurize an interior portion 85 and drive the portions 84 radially outward overcoming any memory characteristics of the inner lamination 81. This produces a configuration essentially shown in FIG. 14 in which both the first surfaces 83 and the second surfaces 84 contact the vessels. In this configuration the frictional characteristics of the surface coatings 84 essentially determine the sliding frictional characteristics of the expansible device 80 in its expanded state.

FIGS. 13 and 14 therefore disclose a structure that differs from that shown in FIGS. 1 through 12 because in the compact state as shown in FIG. 13 the expansible device exposes only the first coating portions 83 by positioning the second portions 84 in a radially depressed area as opposed to actually folding the second areas under the first areas. However, the effect is the same. That is, the first portions 83 essentially establish the frictional characteristics of the structure in the compact state. Contact between the adjacent vessels and the second portions 84 in the compact configuration shown in FIG. 13 occur with minimal normal force so that any friction is generated with the surfaces 84 is minimal in the compact state.

Figure 15:
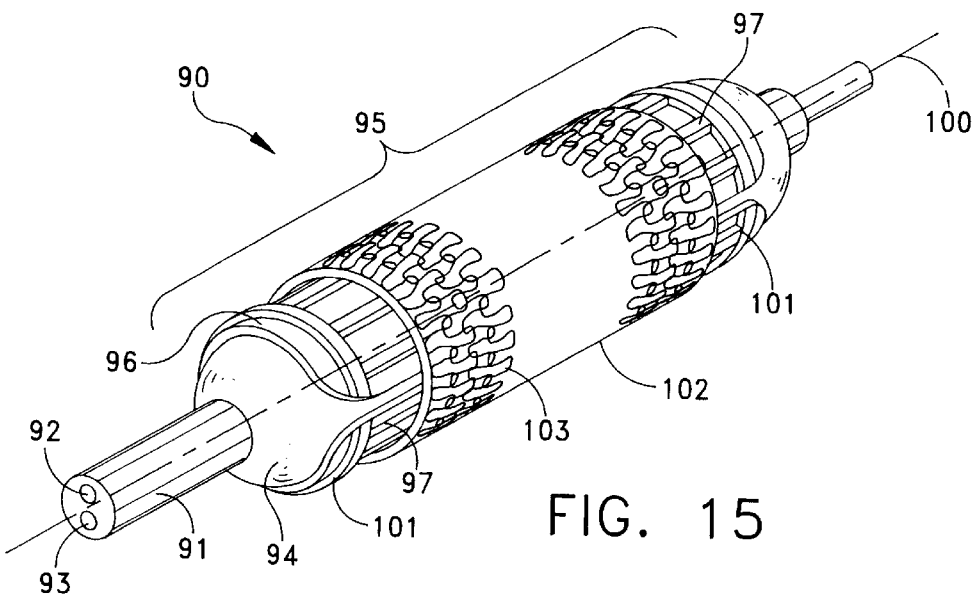
FIG. 15 is a perspective view of an alternate form of the balloon catheter in FIG. 1 specially adapted for use in a stent delivery system.

FIG. 15 depicts a balloon catheter 90 of the general type shown in FIG. 1 in its compact orientation for use in a stent delivery application. In this case a catheter 91 with an optional guidewire lumen 92 and inflation lumen 93 carries an expansible balloon 94 at a distal end 95. The balloon 94 in FIG. 15 is folded to define a continuous first material portion 96 with an integral exterior surface that is treated to have a coefficient of friction that is greater than the coefficient of friction for the exterior surface of the remaining portion of the balloon. In this particular embodiment a ribbing structure such as shown in FIG. 8 incorporates axial ribs 97 that parallel a balloon axis 100 and circumferentially extending ribs 101. The remaining portion of the balloon is smooth so that the pattern of ribs 97 and 101 across the first portion 96 provide an increased friction across the first surface. As will be apparent, any surface treatment could provide the same increased frictional characteristic for the first portion as the ribs 97 and 101 provide.

In its compacted state, the balloon catheter 80 carries an expansible stent 102 in its contracted state. Such stents are well known in the art and are characterized as self-expanding and non-self-expanding stents. Non-self-expanding stents require a force for displacement into an expanded state. The stent construction which may comprise, as shown in FIG. 15, interlocked loops 103 of filamentary material react by locking the stent 102 in its expanded state once it reaches that position.

Figure 16:
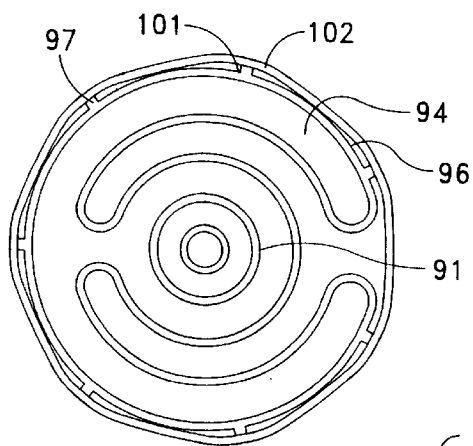
FIG. 16 is a transverse cross-section through the balloon catheter of FIG. 15, when the balloon and stent are in their contracted or compact states.
Figure 17:
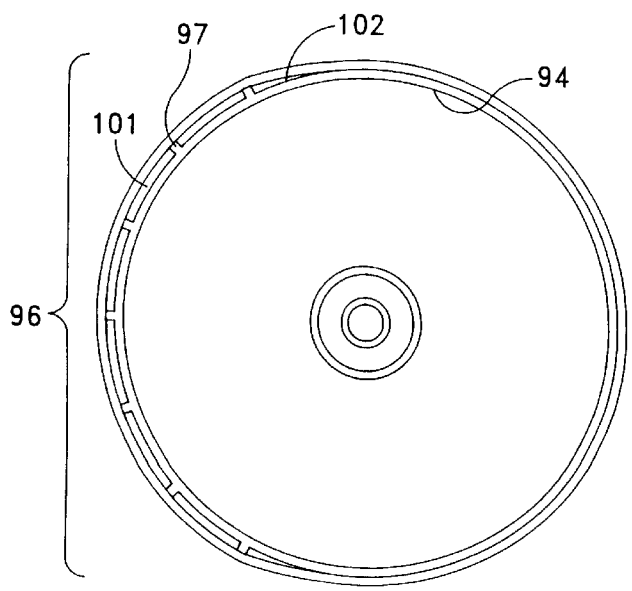
FIG. 17 is a transverse cross-section of the balloon catheter in FIG. 15 in an inflated or expanded state.

The operation of this system can be better understood by referring to FIGS. 16 and 17. FIG. 16 shows the balloon 94 formed about the catheter 91 and shows that the balloon is folded in the same way as shown in FIGS. 1 and 2. In this particular implementation, however, the exterior surface presented by the balloon has formed the longitudinal ribs 97 and circumferential ribs 101 about the first surface 96. Thus in the contracted state the stent 102 meshes with the ribs 97 and 101, and the ribs 97 and 101 effectively grip the stent 102 so it will not slide longitudinally or circumferentially as the balloon catheter 90 with the stent 102 move to a final site even without any overlying sheath.

When an inflation fluid is injected through the inflation lumen 93, the balloon 94 expands into the position shown in FIG. 17. In this position, the stent 102 locks into its expanded form. Slight deflation of the balloon will relax the radial force exerted by the ribs 97 and 101 and the frictional characteristics of the balloon will then become dominated by the second portion of the balloon that is free of any such rib structures. This facilitates release from the stent 102 and further collapse of the balloon allows its withdrawal. In some cases the balloon may undergo a random folding to minimize the areas that are exposed by the ribs 97 and 101 so that even in the collapsed condition the frictional characteristics of any exposed surfaces of the second portion will reduce the overall frictional characteristics of the balloon. However, the balloon 94 is readily removed even if it returns to the state shown in FIG. 15 on collapse because the overall diameter of the balloon 94 will be less than the combined diameters of the balloon 94 and the stent 102 during delivery.

In each of the specifically disclosed embodiments and in other evident variations a balloon catheter in its compact or deflated form produces a balloon configuration with one coefficient of friction during the transfer of the balloon to and across a lesion and another when the balloon expands. In some embodiments expansion produces at least one section having a surface with a higher coefficient of friction that dominates and increases the overall coefficient of friction for the balloon because this surface is greater than the surface exposed when the balloon is uninflated. This stabilizes the balloon in a lesion and minimizes the chances for its unwanted longitudinal displacement. In others, as are useful in stent delivery systems, the higher friction is produced when the balloon is compacted.

This invention has been disclosed in terms of certain embodiments. It will be apparent that many modifications, particularly in the form of different coatings and surface treatments can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. A medical balloon that is expansible from a compact state to an expanded state in a patient's vessel, the exterior surface of said balloon being formed with first and second exterior surface portions, said balloon, in its compact state, essentially exposing only said first exterior surface portions and, in its expanded state, exposing both said first and second exterior surface portions, said first and second external surface portions being conformed with said balloon to have first and second permanent coefficients of sliding friction, respectively, the first and second permanent coefficients of sliding friction being different whereby the first permanent coefficient of sliding friction is determinative of the characteristic of sliding friction when said balloon is in its compact configuration and the second permanent coefficient of sliding friction is substantially determinative of the overall characteristic of sliding friction when said balloon is in its expanded state.

2. A medical balloon as recited in claim 1 wherein said balloon lies along an axis and one of said first and second exterior surface portions is formed with spaced ribs that extend circumferentially about the axis thereby to produce an exterior surface portion with a greater coefficient of sliding friction than the coefficient of sliding friction for the other of said exterior surface portions.

3. A medical balloon as recited in claim 2 wherein said ribbed surface additionally includes spaced ribs that extend parallel to the axis and intersect said circumferentially extending ribs.

4. A medical balloon as recited in claim 1 wherein the exterior surface portion of one of said first and second exterior portions comprises a permanent external coating that provides a permanent coefficient of sliding friction that differs from the permanent coefficient of friction for said other exterior surface portion.

5. A medical balloon as recited in claim 4 wherein the exterior surface of the other of said exterior surface portions comprises another permanent coating.

6. A medical balloon as recited in claim 1 wherein the first permanent coefficient of sliding friction is less than the second permanent coefficient of sliding friction.

7. A medical balloon as recited in claim 1 wherein the first permanent coefficient of sliding friction is greater than the second permanent coefficient of friction.

8. A medical balloon as recited in claim 1 wherein one of said first and second exterior surface portions is textured to have a greater permanent coefficient of sliding friction than the permanent coefficient of sliding friction for the other of said exterior surface portions.

9. A balloon catheter for insertion in a patient's vessels comprising:

A) a catheter having a lumen therein, and

B) an expansible balloon operatively connected with said lumen for selective inflation between compact and expanded conditions, said balloon operatively carried on said catheter with an exterior surface being formed with first and second exterior surface portions, said balloon, in its compact state, essentially exposing only said first exterior surface portions and, in its expanded state, exposing both said first and second exterior surface portions, said first and second exterior surface portions being conformed with said balloon to have first and second permanent coefficients of sliding friction, respectively, the first and second permanent coefficients of sliding friction being different whereby the first permanent characteristic of sliding friction is determinative of the characteristic of sliding friction when said balloon is in its compact configuration and the second permanent characteristic of sliding friction is substantially determinative of the overall characteristic of sliding friction when said balloon is in its expanded state.

10. A balloon catheter as recited in claim 9 wherein said balloon lies along an axis and one of said first and second exterior surface portions is formed with spaced ribs that extend circumferentially about the axis whereby one of said first and and second exterior surface portions has a greater permanent coefficient of sliding friction than the other of said first and second exterior surface portions.

11. A balloon catheter as recited in claim 10 wherein said ribbed surface additionally includes spaced ribs that extend parallel to the axis and intersect said circumferentially extending ribs.

12. A balloon catheter as recited in claim 9 wherein one of said first and and second exterior surface portions comprises a permanent external coating that provides a permanent coefficient of sliding friction that differs from the permanent coefficient of sliding friction of the other of said exterior surface portions.

13. A balloon catheter as recited in claim 12 wherein said other of said first and second exterior surface portions comprises another permanent coating having a permanent coefficient of sliding friction that differs from the permanent coefficient of sliding friction produced by said coating on the one exterior surface portion.

14. A balloon catheter as recited in claim 9 wherein the first permanent coefficient of sliding friction is less than the second permanent coefficient of sliding friction.

15. A balloon catheter as recited in claim 9 wherein the first permanent coefficient of sliding friction is greater than the second permanent coefficient of sliding friction.

16. A balloon catheter as recited in claim 9 wherein one of said first and second exterior surface portions is textured to have a greater permanent coefficient of sliding friction than the other of said first and second exterior surface portions.

* * * * *